(12) United States Patent
Doser (10) Patent No.: US 11,607,106 B2
(45) Date of Patent: Mar. 21, 2023

(54) ENDOSCOPE PROXIMITY SENSOR (71) Applicant: Schölly Fiberoptic GmbH, Denzlingen (DE)

(72) Inventor: Ingo Doser, Villingen-Schwenningen (DE)

(73) Assignee: SCHÖLLY FIBEROPTIC GMBH, Denzlingen (DE)

(*) Notice: Subject to any disclaimer, the term of this patent is extended or adjusted under 35 U.S.C. 154(b) by 1304 days.

(21) Appl. No.: 16/001,379

(22) Filed: Jun. 6, 2018

(65) Prior Publication Data
US 2019/0000302 A1 Jan. 3, 2019

(30) Foreign Application Priority Data
Jun. 28, 2017 (DE) .................. 102017114 410.2

(51) Int. Cl.
A61B 5/06 (2006.01)
A61B 1/00 (2006.01)
A61B 1/05 (2006.01)
A61B 5/00 (2006.01)

(52) U.S. Cl.
CPC ...... *A61B 1/00006* (2013.01); *A61B 1/00055* (2013.01); *A61B 1/00066* (2013.01); *A61B 1/00097* (2022.02); *A61B 1/05* (2013.01); *A61B 5/065* (2013.01); *A61B 1/00163* (2013.01); *A61B 5/061* (2013.01); *A61B 5/6886* (2013.01); *A61B 2562/0257* (2013.01)

(58) Field of Classification Search
CPC . A61B 5/061; A61B 2562/0257; A61B 5/065; A61B 1/0008
See application file for complete search history.

(56) References Cited

U.S. PATENT DOCUMENTS

| 6,547,757 B1* | 4/2003 | Kranz | A61B 5/6886 600/478 |
| 9,119,552 B2 | 9/2015 | Baumann et al. | |
| 2012/0147708 A1* | 6/2012 | Lee | G01S 15/04 367/180 |
| 2013/0003078 A1* | 1/2013 | Hart | G01B 11/24 356/601 |
| 2015/0282695 A1* | 10/2015 | Tay | A61B 1/126 600/124 |
| 2016/0022154 A1* | 1/2016 | Warnking | A61B 5/6851 600/486 |
| 2017/0196478 A1* | 7/2017 | Hunter | A61B 5/6847 |

FOREIGN PATENT DOCUMENTS

| DE | 19936904 | 2/2001 |
| DE | 102011119608 | 5/2013 |

* cited by examiner

Primary Examiner — Anh Tuan T Nguyen
Assistant Examiner — Rynae E Boler
(74) Attorney, Agent, or Firm — Volpe Koenig (57) ABSTRACT An endoscope (1) with a shaft (2), a grip (3) connected to the shaft (2) at a proximal end region of the shaft (2), and a viewing region (4) formed in a distal end region of the shaft (2) by optical elements. The shaft (2) has at least one proximity sensor (5), of which the measuring region lies at least outside the viewing region (4), preferably in such a way that the measuring region of the proximity sensor (5) covers at least the distance of the lateral region of the distal end region. The endoscope has an evaluation device (6) which is configured to generate a warning signal when a definable distance threshold value is undershot.

15 Claims, 4 Drawing Sheets

ENDOSCOPE PROXIMITY SENSOR

INCORPORATION BY REFERENCE

The following documents are incorporated herein by reference as if fully set forth: German Patent Application No. 10 2017 114 410.2, filed Jun. 28, 2017.

BACKGROUND

The invention relates to an endoscope with a shaft, a grip connected to the shaft at a proximal end region of the shaft, and a viewing region formed in a distal end region of the shaft.

Endoscopes of this kind are already known and are used to perform or to monitor operations in difficulty accessible cavities of a patient's body.

In such operations there is the problem that unwanted contact may occur between the endoscope and the tissue that forms the cavity. In particular, contact between the tissue and the endoscope tip located at a distal end is disadvantageous since it may cause damage to the tissue. Moreover, contact between the endoscope tip and the tissue can also lead to soiling of the optical components that form the viewing region. The function of the endoscope may thus be impaired, which is a disadvantage during an examination or an operation.

SUMMARY

The object is therefore to make available an endoscope of the aforementioned type with which the stated disadvantages can be avoided.

This object is achieved with an endoscope having one or more features of the invention. In particular, in order to achieve the stated object according to the invention in an endoscope of the above-described type, provision is made that the shaft has at least one proximity sensor, of which the measuring region lies at least outside the viewing region, and that the endoscope has an evaluation unit which is configured to generate a warning signal when a definable distance threshold value is undershot. The distance threshold value can be a predefined value, which can be stored in a lookup table in the evaluation unit. By use of the endoscope according to the invention, it is therefore possible to prevent unwanted contact between the shaft of the endoscope and the patient's tissue that is to be examined. Depending on what examination or operation is performed, it is possible to predefine a different distance threshold value that is not to be undershot. However, if the value is undershot, a warning signal is generated which draws the attention of the person using the endoscope to the danger of contact with the tissue. It is thus possible for the user to once again establish a sufficient safety distance between tissue and endoscope well before the occurrence of contact between endoscope and tissue. By use of the endoscope according to the invention, the danger of a collision between the endoscope and the tissue is therefore greatly reduced compared to conventional endoscopes of the type mentioned at the outset. The measuring region of the at least one proximity sensor preferably lies exclusively outside the viewing region of the endoscope. According to a further advantageous embodiment, provision can be made that the measuring region of the at least one proximity sensor and the viewing region of the endoscope overlap each other, or that the measuring region of the at least one proximity sensor completely covers the viewing region of the endoscope.

It may be particularly expedient if the at least one proximity sensor is arranged or formed at least at the distal end of the shaft. In particular, provision can be made according to the invention that the at least one proximity sensor is arranged or formed exclusively at the distal end of the shaft. It is thereby possible to prevent a lateral part of the distal end of the shaft, i.e. an endoscope tip, coming into contact with the tissue, although this part of the endoscope tip lies outside the viewing region of the endoscope. It may be particularly expedient if a first electrode region of the at least one proximity sensor is arranged or formed at least or exclusively at the distal end of the shaft.

According to a particularly advantageous embodiment of the endoscope according to the invention, provision can be made that the proximity sensor is configured as a capacitive sensor, with at least one or the aforementioned electrode region, and that a second electrode region is formed by ground, i.e. preferably by a patient's body connected to ground. Between the first electrode region and the second electrode region, there is therefore an electric field whose capacitance varies according to the distance between proximity sensor and tissue. By determination of the capacitance, it is possible to determine the distance between endoscope and tissue by matching to a characteristic curve stored in the evaluation device. In particular, the endoscope has a high-frequency alternating voltage source, which is in the megahertz range and supplies the proximity sensor, and/or a measurement device, in particular a demodulator. By use of the measurement device, an amplitude of the voltage is measurable which varies according to the tissue connected to ground.

In order to limit the measuring region of the proximity sensor to the distal portion of the endoscope, in particular of the endoscope tip, provision can be made that the shaft has a shield which is electrically insulated from a or the aforementioned electrode region of the proximity sensor, wherein the shield is made of electrically conductive material, in particular of metal. A connection line of the proximity sensor can thus be shielded, such that no or fewer electric or magnetic fields interfering with the measurement act on the connection line of the proximity sensor. The shield preferably extends from a proximal end of the shaft as far as the at least one proximity sensor.

It may also be expedient if the grip is made of an electrically conductive material, in particular of metal, and is electrically insulated from the shaft and/or electrically insulated from a or the aforementioned first electrode region, in particular from the endoscope tip.

According to a further advantageous embodiment of the endoscope according to the invention, it may be expedient that at least two first electrode regions, in particular several first electrode regions, of several proximity sensors are arranged along the shaft, lying behind one another and in particular electrically insulated from one another. These electrode regions can each be configured such that independent distance measurements can be carried out between the individual proximity sensors and the tissue that forms the cavity. In this way, it is possible to differentiate between which region of the shaft and the tissue there is a threat of contact. Thus, the entire lateral region of the shaft can be monitored in terms of its distance from the tissue. The individual segments of the shaft with the proximity sensors each have their own connection lines for each proximity sensor, which lines are preferably shielded from the outside by a shield. An insulator is arranged between the individual segments with the proximity sensors, as a result of which the segments are electrically separated from each other. It is thereby possible for independent distance measurements to be carried out by the respective proximity sensors. Provision can also be made that each proximity sensor forms a shield for a connection line of a succeeding proximity sensor in the distal direction, for example the aforementioned shield.

To be able to more easily examine different regions within a cavity, it may be expedient if an endoscope tip region, movable relative to the shaft, is formed at the distal end of the shaft, such that the viewing region of the endoscope and/or the measuring region of the at least one proximity sensor arranged at the distal end of the shaft can be varied by moving the endoscope tip region. It is thereby possible to bring different regions of the cavity into the viewing region of the endoscope without completely changing the position of the whole shaft. By use of the proximity sensor, it is possible to prevent the movable endoscope tip from accidentally being brought into contact with the tissue, since the proximity sensor is arranged in the movable endoscope tip region. The measuring region of the proximity sensor thus also covers the regions that are not covered by the viewing region of the endoscope. In addition, the movable endoscope tip affords the advantage that regions of the cavity can be examined that cannot be brought into the viewing region of an endoscope with a rigid endoscope tip, since the movable tip is adjustable relative to a longitudinal axis of the shaft by an angle, in particular an angle of at least 60°, preferably 90°.

It may be particularly expedient if the proximity sensor is configured to measure a first signal which is dependent on the capacitance to be measured between a or the aforementioned first electrode region and a or the aforementioned second electrode region. It may be particularly expedient if the first electrode region is formed by the proximity sensor and the second electrode region is formed by the ground, that is to say the patient's body to ground. According to one or more further advantageous embodiments, it may be advantageous if the first signal is dependent on the capacitance between an endoscope tip and the shaft and/or between the endoscope tip and the ground and/or between the shaft and the ground. The first electrode region is preferably formed at an endoscope tip.

To be able to better avoid measurement inaccuracies, it may be expedient if at least one second signal for determining a differential signal between the first signal and the at least one second signal is measured by a further or the aforementioned proximity sensor, in particular wherein the at least one second signal depends on a further capacitance between the shaft and the patient's body to ground and/or between the grip and the patient's body to ground and/or between the shaft and the grip. Measurement inaccuracies can arise in particular from a parasitic capacitance which electrically couples the shaft and the first electrode region and/or the shaft and the grip. The first and/or the second signal can be a voltage and/or a current. The first signal and second signal is preferably the amplitude of an alternating voltage.

It may therefore be particularly expedient if, in order to determine a capacitance to be measured between a or the aforementioned electrode region and a or the aforementioned second electrode region, the endoscope according to the invention is configured to measure at least one further capacitance which is electrically coupled by a parasitic capacitance to the capacitance that is to be measured.

In order for the user to notice in good time that a critical distance between endoscope and tissue has been undershot, it may be expedient if the evaluation device is configured to generate an acoustic and/or visual warning signal when the definable distance threshold value is undershot.

In order to provide the operator of the endoscope with visual and/or acoustic feedback in the event of the distance threshold value being undershot, it may be advantageous if the at least one warning signal is set up to vary according to the distance. The warning signals can in particular vary in such a way that a warning signal frequency is higher the shorter the distance between the endoscope and a or the patient's body. The operator of the endoscope can thus more accurately estimate whether there is an immediate danger of collision or whether there is still a sufficient distance between the endoscope and the patient's body.

In order to achieve the aforementioned object, the invention further relates to a method for preventing a collision between an endoscope and tissue, wherein a measurement of a distance between the endoscope, in particular an endoscope tip, and at least one tissue outside the viewing region of the endoscope is carried out continuously by a proximity sensor at least at the distal end of a shaft of the endoscope, wherein a warning signal is generated when a threshold value defining a critical distance value from the tissue is attained or undershot, and wherein the distance between the tissue and the endoscope tip is increased via the critical distance value.

In order to increase the measurement accuracy, it may be expedient if a capacitive sensor is used for the distance measurement, and if, in addition to a first capacitance to be measured between the proximity sensor and the tissue, at least one further capacitance is measured which is electrically coupled by a parasitic capacitance to the capacitance that is to be measured.

The invention relates to an endoscope with a shaft, a grip connected to the shaft at a proximal end region of the shaft, and a viewing region formed in a distal end region of the shaft by optical elements. The shaft has at least one proximity sensor, of which the measuring region lies at least outside the viewing region, preferably in such a way that the measuring region of the proximity sensor covers at least the distance of the lateral region of the distal end region. The endoscope has an evaluation device which is configured to generate a warning signal when a definable distance threshold value is undershot.

BRIEF DESCRIPTION OF THE DRAWINGS

The invention is now explained in more detail on the basis of a number of illustrative embodiments, but it is not limited to these illustrative embodiments. Further illustrative embodiments arise by combining the features of individual or multiple claims with each other and/or with individual or multiple features of the illustrative embodiments.

DETAILED DESCRIPTION

FIGS. 1 to 6 show partially different embodiments of an endoscope 1 according to the invention, in each case with a shaft 2, and a grip 3 connected to the shaft 2 at a proximal end region of the shaft 2. A viewing region 4 is formed at the distal end region of the shaft 2, in particular by optical elements.

FIGS. 1 to 4 and FIG. 6 show only the front region with a part of the grip 3 and the endoscope shaft 2.

Figure 5:
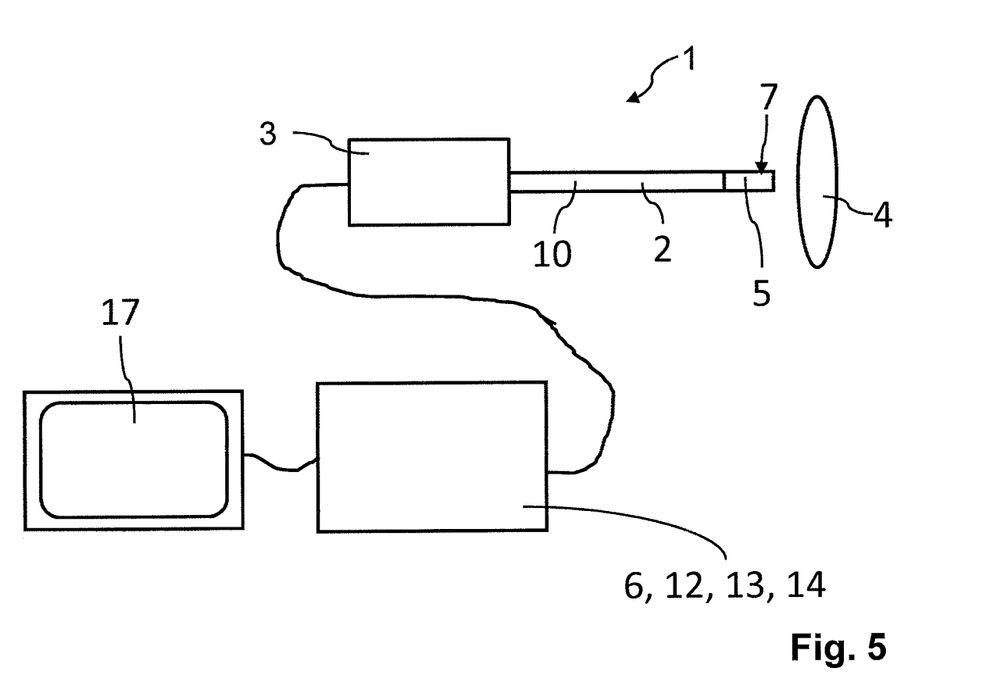
FIG. 5 shows an overall view of the endoscope according to the invention from FIG. 2 in a schematic representation.
Figure 6:
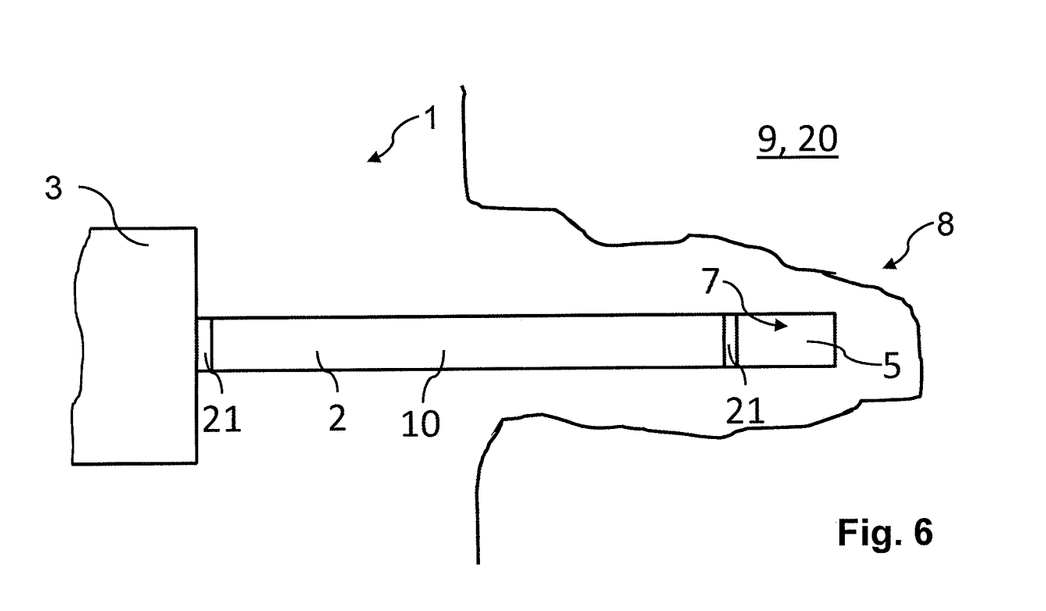
FIG. 6 shows a detail of the shaft and of the grip of the endoscope according to the invention from FIGS. 2 and 5 in the position of use, that is to say that the shaft is at least partially inserted into a cavity.

FIG. 5 shows the whole endoscope 1 according to the invention. FIG. 6 shows the endoscope 1 in the position of use, wherein the shaft 2 of the endoscope 1 has here been at least partially inserted into a cavity formed by a patient's body 20. The patient's body 20 is connected to ground 9.

The endoscope 1 has a proximity sensor 5 for determining a distance of the part of the endoscope 1 inserted into the cavity or of a partial section of the inserted part, the measuring region of which proximity sensor 5 lies at least outside the viewing region 4. The proximity sensor 5 measures the distance between the inserted part of the endoscope 1 or of a partial section thereof and the tissue that forms the cavity. It is thus possible to prevent unwanted collision of the endoscope 1 with the tissue, which can lead, for example, to damage of the tissue and/or contamination of the optical components of the endoscope 1 at the distal end of the shaft 2.

In order to ensure that a person using the endoscope 1 is informed at an early stage that a critical distance value has been undershot, the endoscope 1 according to the invention has an evaluation device 6 which is configured to generate a warning signal when a definable distance threshold value is undershot. The distance threshold value is freely definable and can be stored in the evaluation device 6.

A particularly expedient embodiment of the endoscope 1 has a proximity sensor 5 configured as a capacitive sensor. The proximity sensor 5 has at least one electrode region 7. A second electrode region 8 is formed by ground 9. In the case of examination of a cavity, the ground 9 is formed by the patient's body 20, which is connected to ground 9. By measuring the capacitance between the first electrode region 7 and the ground 9, a conclusion can be reached regarding the distance between the proximity sensor 5 and the tissue. A capacitance C between the first electrode region 7 and the second electrode region 8, that is to say the ground 9, is greater the closer the proximity sensor 5 is to the tissue. Conversely, the capacitance decreases when the distance between the first electrode region 7 and the second electrode region 8 is increased.

In the endoscope 1 shown in FIGS. 2, 4, 5, and 6, the proximity sensor 5 and the respective first electrode region 7 are arranged at the distal end of the shaft 2. The shaft 2 therefore has a multi-part design, wherein the individual segments are electrically insulated from one another by an insulator 21. This makes it possible to determine the distance of the electrode tip at the distal end of the shaft 2 from the patient's body 20. Optionally, the shaft 2 and/or the grip 3 can have or form a further proximity sensor 5.

Figure 1:
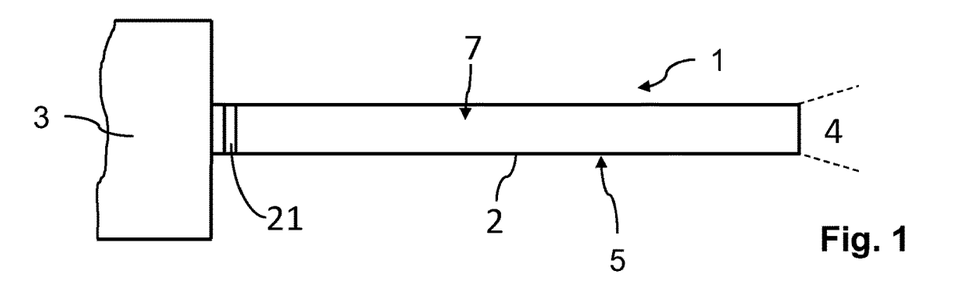
FIG. 1 shows a detail of a schematic view of an embodiment of the endoscope according to the invention, wherein the proximity sensor is formed by the shaft.
Figure 2:
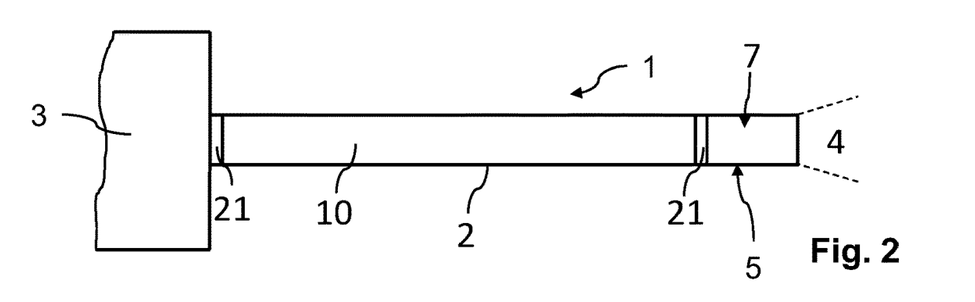
FIG. 2 shows a detail of a schematic view of a further embodiment of the endoscope according to the invention, wherein the proximity sensor is arranged at the distal end on an endoscope tip.

The endoscope 1 shown in FIG. 1 has a shaft 2, and the shaft 2 forms the proximity sensor 5 and the first electrode region 7. The distance between the shaft 2 and the patient's body 20 can thus be determined. Arranged between the shaft 2 and the grip 3 is an electrical insulator 21 which electrically separates the shaft 2 and the grip 3. The endoscope 1 shown in FIGS. 2, 4, 5 and 6 has a shaft 2 with an electric shield 10. The shield 10 is here made of electrically conductive material, in particular of metal. It serves as a shield for a connection line of the proximity sensor 5 which, in the embodiments shown, is in each case arranged at the distal end region of the shaft 2. The measuring region of the proximity sensor 5 is in this case at least configured such that it also covers regions lying outside the viewing region 4. An electrical insulator 21 is arranged between the proximity sensor 5, arranged at the distal end region of the shaft 2, and the shaft 2, in particular the shield 10. Moreover, a further electrical insulator 21 is arranged between the grip 3 and the shaft 2, in particular the shield 10. By virtue of the shield 10 and the insulator 21 between the shaft 2 and the distal end region, it is possible for the measuring region of the proximity sensor 5 to be limited to the distal end region of the shaft 2. The shield 10 can itself form a further proximity sensor, as is explained with reference to FIG. 8.

Figure 3:
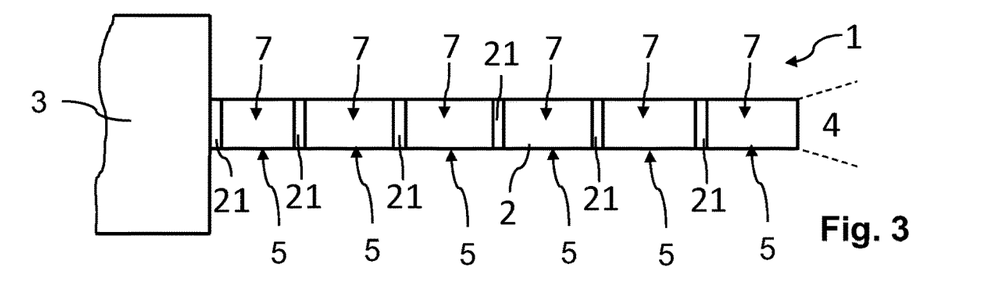
FIG. 3 shows a detail of a schematic view of a further embodiment of the endoscope according to the invention, wherein the shaft is divided into several segments lying behind one another, which segments each have a proximity sensor and are electrically insulated from one another.

FIG. 3 shows a further embodiment of the endoscope 1 according to the invention, in which the shaft is divided into several segments which are separated from one another in each case by an insulator 21. A proximity sensor 5 with a first electrode region 7 is arranged or formed in each segment. By virtue of the proximity sensors 5 being arranged behind one another and being provided in each case with their own connection lines, independent measurements of the distance to the patient's body 20 can be carried out. It is thus possible to more precisely determine which region of the shaft 2, in particular which segment, has been moved too close to the tissue of the patient's body 20. The number of proximity sensors 5 shown is only illustrative. They can be present in a greater or smaller number. Each proximity sensor 5 can form a shield for the connection lines of the respectively subsequent proximity sensor in the distal direction.

Figure 4:
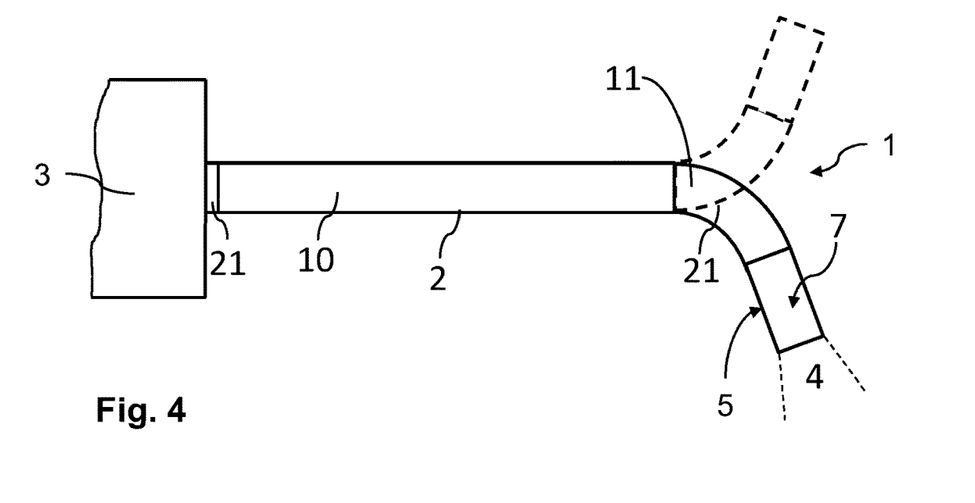
FIG. 4 shows a detail of a schematic view of an embodiment of the endoscope according to the invention, wherein the endoscope has a movable shaft tip, and the proximity sensor is arranged in the movable shaft tip.

FIG. 4 shows a further embodiment of the endoscope 1 according to the invention, in which an endoscope tip region 11, which is adjustable relative to the shaft 2, is formed at the distal end of the shaft 2. The adjustable, i.e. movable, endoscope tip region 11 can be adjusted, for example, by use of a control arranged at the grip 3. It is thereby possible to modify the viewing region 4 of the endoscope 1 without the shaft 2 having to be moved as a whole. The measuring region of the proximity sensor 5 arranged at least at the distal end of the shaft 2 is likewise modified by the movement of the endoscope tip region 11, such that the distance of the endoscope tip region 11 from the tissue of the patient's body 20 can still be detected. The endoscope tip region 11 can be deflected with respect to a longitudinal axis of the shaft, preferably in all directions, by an angle, in particular an angle of at least 60°, preferably at least 90°.

The evaluation device 6, which can be configured for example as a combination of demodulator 12, analog-digital converter 13 and controller 14, is set up to generate an acoustic and/or visual warning signal when the defined distance threshold value is undershot. The distance threshold value can be stored in the evaluation device, for example as a look-up table.

Figure 7:
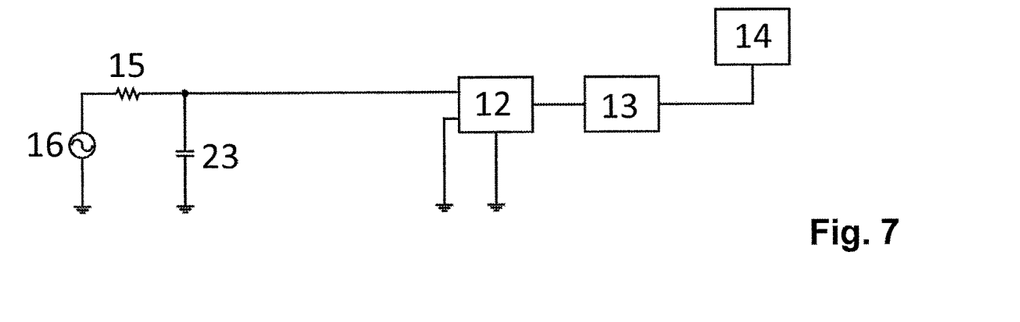
FIG. 7 shows a circuit diagram of an embodiment of the endoscope according to the invention from FIG. 1, wherein a signal is measured, said signal being dependent on the capacitance between shaft and ground.

The circuit diagram in FIG. 7 relates to the endoscope according to FIG. 1. Here, a fixed frequency, in particular in the megahertz range, is generated by a high-frequency alternating voltage source 16 and applied to the shaft 2. By an ohmic resistance 15 at the output of the alternating voltage source 16, a voltage divider is formed together with a capacitance $C_{Shaft}$ 23 in order to prevent unwanted stray currents. High-frequency signals from the alternating voltage source 16 are measurable by the demodulator 12, wherein an amplitude depends on the distance of the first electrode region 7 from the patient's body 20. The capacitance $C_{Shaft}$ 23 is greater the closer the shaft 2 is located to the tissue of the patient's body 20. Correspondingly, the measurable amplitude increases when the distance decreases.

The demodulator 12 taps the signal at the capacitance 23, measures the amplitude and increases it in such a way that a distance value can be converted with the analog-digital converter. The demodulator 12 converts the high-frequency signal to a low-frequency signal. Under stationary conditions, that is to say neither the endoscope 1 nor the patient's body 20 moves relative to the ground 9, the demodulator 12 generates a direct voltage. The measured value is then transmitted by the analog-digital converter 13 to the controller 14, which provides the user with a distance value or feedback.

Figure 8:
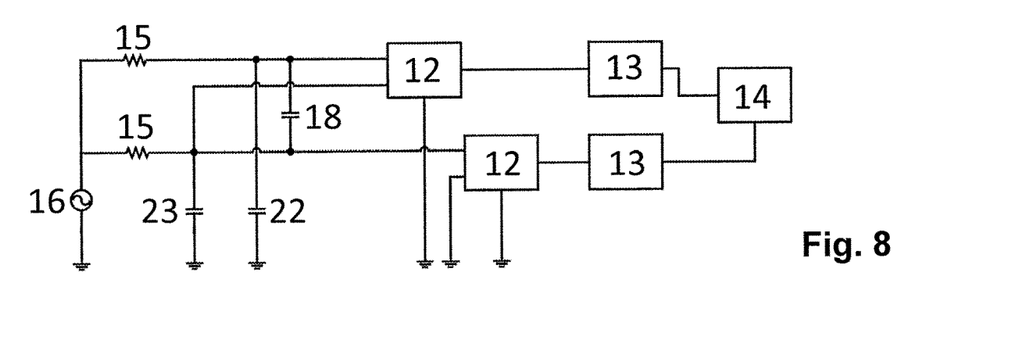
FIG. 8 shows a circuit diagram of an embodiment of the endoscope according to the invention from FIG. 2, wherein, in addition to the signal mentioned with reference to FIG. 7, a further signal is measured which is dependent on the capacitance between ground and endoscope tip.

In the circuit diagram shown in FIG. 8, the endoscope 1 has two proximity sensors 5 which measure signals for a capacitance $C_{Shaft}$ 23 between shaft 2 and ground 9 and a capacitance $C_{Tip}$ 22 between electrode tip and ground 9. Thus, for example, the shield 10 which the shaft 2 forms can be used as a further proximity sensor 5. The endoscope 1 in this case has a demodulator 12 for each proximity sensor 5. Between the endoscope tip and the shaft 2, a parasitic capacitance $C_{Para-Tip-shaft}$ occurs which is generally constant and electrically couples the two capacitances $C_{Shaft}$ 23 and $C_{Tip}$ 22. In order to form a differential signal between the measured signals, so as to measure only the distance between the distal end region, i.e. the endoscope tip, and the patient's body 20 to ground 9, one of the demodulators 12 for the endoscope tip is not routed to ground as shown in FIG. 7 but instead connected to the shaft 2. A parasitic capacitance $C_{Para-Tip-Shaft}$ 18 between endoscope tip and shaft 2 and a capacitance $C_{Shaft}$ 23 between shaft and ground 9 are each much greater than a capacitance $C_{Tip}$ 22 of the endoscope tip and the tissue of the patient's body 20 to ground 9, since the first electrode region 7 of the proximity sensor 5 at the distal end region has a much smaller surface area. For this reason, a differential signal of the measured amplitude signals has to be formed by the controller 14 in order to be able to determine the capacitance $C_{Tip}$ 22. The proximity sensor 5 for the shaft 2 is configured as in FIG. 7 and has its own demodulator 12. According to an alternative embodiment, the proximity sensor 5 can also be omitted in the embodiment of the endoscope 1 according to the invention shown in FIG. 8.

Figure 9:
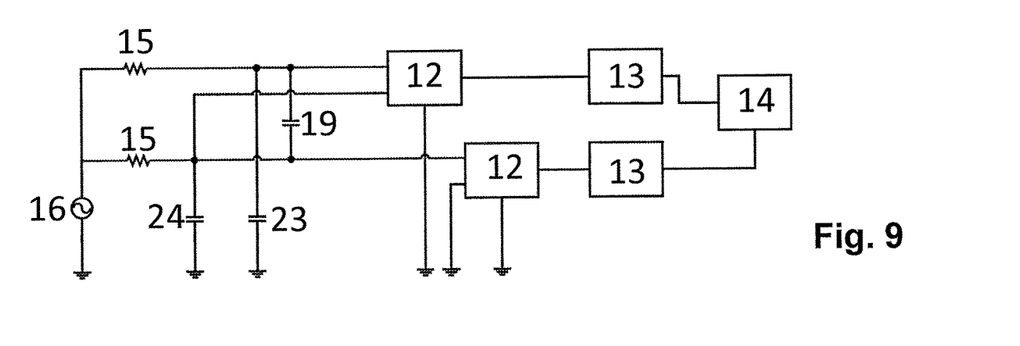
FIG. 9 shows a circuit diagram of a further embodiment of an endoscope according to the invention, wherein the signals that are dependent on the capacitances between ground and shaft and between grip and ground are measured in order to determine the distance.

An embodiment of the endoscope 1 according to the invention with two proximity sensors 5 is again shown in FIG. 9. In contrast to the endoscope 1 shown in FIG. 8, a distance measurement is carried out not by measurement of a signal that depends on the capacitance between endoscope tip and ground, but instead by measurement of a signal that depends on the capacitance $C_{Shaft}$ 23 between shaft 2 and ground 9. The second signal determined is the capacitance $C_{Grip}$ 24 between grip 3 and ground 9. The determination of the capacitance $C_{Grip\ 24}$ serves to eliminate interference of the grip 3 itself and/or of the hand holding the grip 3 or of a stand holding the grip 3. The grip 3 is in this case conductive. Preferably, the grip 3 is made at least partly of metal. According to further embodiments, the grip 3 can be made of plastic and metal, preferably wherein the handgrip 3 has a shield which sits in a plastic housing. The insulating distance between shaft 2 and grip 3 is defined by the insulator 21. Due to a parasitic capacitance $C_{Para-Shaft-Grip}$ 19 between shaft 2 and grip 3, a signal can crosstalk between grip 3 and shaft 2, which in this case also leads to a measurement inaccuracy of the distance value from shaft to tissue. In order to form a differential signal, so as to measure only the distance between the shaft 2 and the patient's body 20 to ground 9, one of the demodulators 12 for the shaft 2 is connected to the grip 3. The second demodulator 12 for the grip 3 measures the signal for the capacitance $C_{Grip}$ 24 to ground 9.

Figure 11:
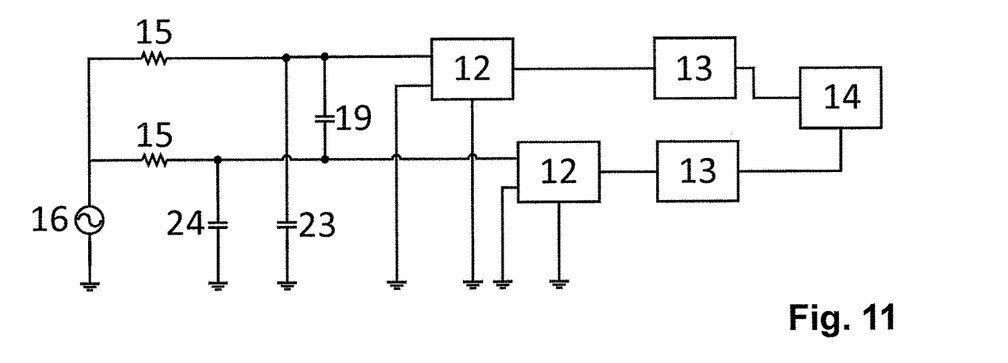
FIG. 11 shows a circuit diagram of a further embodiment of an endoscope according to the invention, wherein the signals that are dependent on the capacitances between ground and shaft and between grip and ground are measured in order to determine the distance.

According to an embodiment representing an alternative to the preceding embodiment, shown in FIG. 11 and likewise having two proximity sensors 5, the capacitances $C_{Shaft}$ 23 and $C_{Grip}$ 24 are each measured to ground 9 in order to form a differential signal. Therefore, in contrast to the embodiment according to FIG. 9, the demodulator 12 for the shaft 2 is likewise connected to ground 9 and therefore not connected to the grip 3. In this embodiment of the invention, the differential signal is determined computationally by the controller 14.

Figure 10:
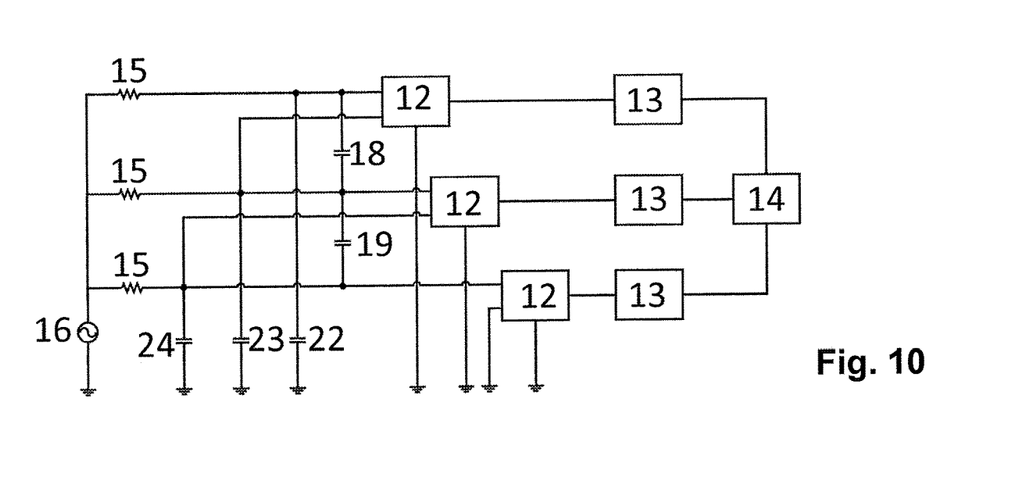
FIG. 10 shows a circuit diagram of a further embodiment of the endoscope according to the invention, wherein three signals are measured here which are dependent on the capacitances between ground and endoscope tip, between ground and shaft and between ground and grip.

FIG. 10 shows a circuit representing a combination of the embodiments shown in FIGS. 8 and 9. The endoscope 1 here has three proximity sensors 5, which determine the capacitances $C_{Tip}$ 22, $C_{Shaft}$ 23 and $C_{Grip}$ 24. Here too, relative measurements are carried out between endoscope tip and shaft 2 and between shaft 2 and grip 3 in order to be able to take account of crosstalk of the signals via the electrical coupling by the parasitic capacitances $C_{Para-Tip-Shaft}$ and $C_{Para-Shaft-Grip}$ in determining the respective distance. In order to form differential signals, the first demodulator 12 for the electrode tip is connected to the shaft 2 to measure $C_{Tip}$ 22. The second demodulator 12 for the shaft 2 for measuring $C_{Shaft}$ 23 is connected to the grip 3, and the third demodulator 12 for the grip 3 measures the signal for the capacitance $C_{Grip}$ 24 to ground 9.

The embodiments of the invention shown in FIGS. 8 to 10 and described here permit a particularly simple structure of the endoscope 1, and yet an efficient elimination of interference effects from parasitic capacitances 18, 19 is possible. In particular, it is not necessary to run a ground line to the endoscope tip, which would lead to an increase in parasitic capacitances 18, 19, in particular between endoscope tip and shaft 2.

Figure 12:
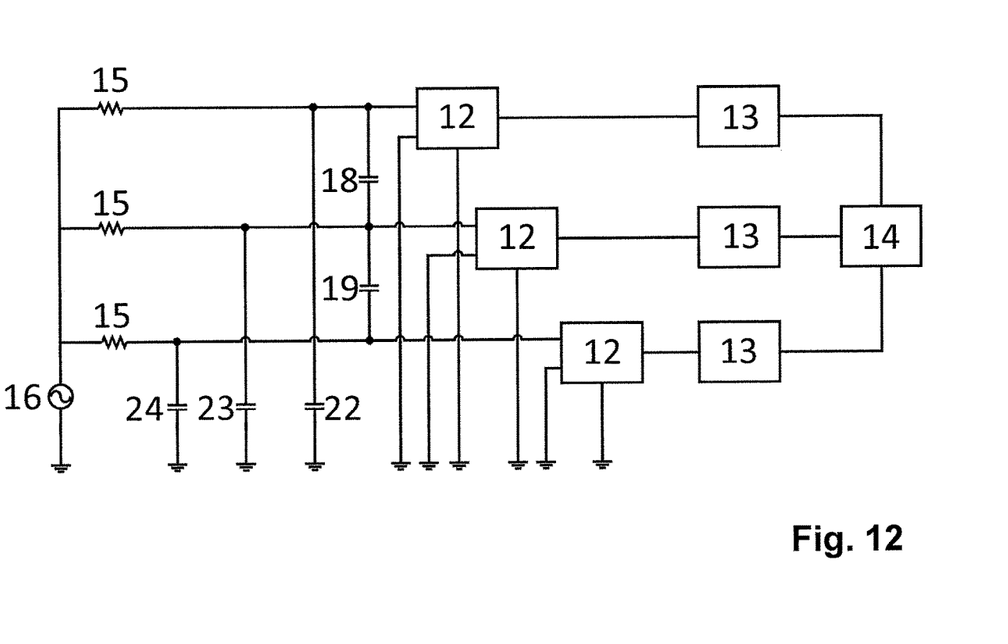
FIG. 12 shows a circuit diagram of a further embodiment of the endoscope according to the invention, wherein three signals are measured here which are dependent on the capacitances between ground and endoscope tip and between the shaft and the grip.

The differential signals for elimination of interference effects by the parasitic capacitances 18, 19 can also be determined or determinable purely computationally by the controller 14. An example of a circuit for computational elimination of interference effects in the capacitance measurements is shown in FIG. 12. Here, all the demodulators 12 of the three proximity sensors 5 are each connected to ground 9. The individual capacitance measurements of $C_{Tip}$ 22, $C_{Shaft}$ 23 and $C_{Grip}$ 24 by the respective proximity sensor 5 are therefore each carried out in relation to ground 9, in order thereafter to eliminate the interference effects, caused by the parasitic capacitances 18, 19, computationally by the controller 14.

It can therefore generally be stated that, in order to determine a capacitance $C_1$ to be measured, in particular between a first electrode region 7 and a second electrode region 8, that is to say the ground 9, at least one further capacitance $C_2$ is measured which is electrically coupled by a parasitic capacitance $C_{Para}$ to the capacitance $C_1$ that is to be measured.

The parasitic capacitance is generally constant, regardless of whether the parasitic capacitance is between endoscope tip and shaft or between shaft and grip. Therefore, the parasitic capacitance can be stored as a constant value.

LIST OF REFERENCE SIGNS 1 endoscope
2 shaft
3 grip
4 viewing region
5 proximity sensor
6 evaluation device
7 first electrode region
8 second electrode region
9 ground
10 shield
11 movable endoscope tip region
12 demodulator
13 analog-digital converter
14 controller
15 ohmic resistance
16 alternating voltage source
17 display
18 parasitic capacitance $C_{Para-Tip-Shaft}$ between endoscope tip and shaft
19 parasitic capacitance $C_{Para-Shaft-Grip}$ between shaft and grip
20 patient's body
21 insulator
22 capacitance $C_{Tip}$ between ground and endoscope tip
23 capacitance $C_{Shaft}$ between ground and shaft
24 capacitance $C_{Grip}$ between ground and grip

The invention claimed is:

1. An endoscope comprising:
a shaft;
a grip connected to the shaft at a proximal end region of the shaft;
a viewing region formed in a distal end region of the shaft;
at least one proximity sensor at the distal end of the shaft, and having a measuring region provided for the shaft, the measuring region lies exclusively outside of the viewing region, wherein the proximity sensor is configured as a capacitive sensor, with at least a first electrode region at the distal end of the shaft, and a second electrode region formed by ground that is adapted to be connected to a patient's body; and
an evaluation device configured to generate at least one warning signal when a definable distance threshold value for the measuring region is undershot.

2. The endoscope as claimed in claim 1, wherein the shaft further comprises a shield which is electrically insulated from the first electrode region of the proximity sensor, and the shield is made of electrically conductive material.

3. The endoscope as claimed in claim 2, wherein the shield is made of metal, and extends from a proximal end of the shaft as far as the at least one proximity sensor.

4. The endoscope as claimed in claim 1, wherein the grip is made of an electrically conductive material, and is electrically insulated from at least one of the shaft or a first electrode region of the at least one proximity sensor.

5. The endoscope as claimed in claim 1, wherein the at least one proximity sensor comprises a plurality of proximity sensors, each having an associated first electrode region such that a plurality of the first electrode regions are arranged along the distal end of the shaft, lying behind one another, and the plurality of the first electrode regions are electrically insulated from one another such that the respective proximity sensors are configured to carry out independent distance measurements.

6. The endoscope as claimed in claim 1, further comprising an endoscope tip region that is movable relative to the shaft formed at the distal end of the shaft, such that at least one of the viewing region of the endoscope or the measuring region of the at least one proximity sensor arranged at the distal end of the shaft are variable by a movement of the endoscope tip region.

7. The endoscope as claimed in claim 1, wherein the at least one proximity sensor is configured to measure a signal, with said signal being dependent on a capacitance between the first electrode region of the at least one proximity sensor and the second electrode region.

8. The endoscope as claimed in claim 7, wherein said signal is dependent on the capacitance between at least one of an endoscope tip and the shaft, the endoscope tip and ground or the shaft and the ground.

9. The endoscope as claimed in claim 7, wherein the at least one proximity sensor is configured to measure at least one second signal for determining a differential signal between the first signal.

10. The endoscope as claimed in claim 9, wherein the at least one second signal depends on a further capacitance between at least one of the shaft and a ground that is adapted to be provided by a patient's body, the grip and a ground that is adapted to be provided by a patient's body, or the shaft and the grip.

11. The endoscope as claimed in claim 1, wherein, in order to determine a capacitance to be measured between the first electrode region of the at least one proximity sensor and the second electrode region, the endoscope is configured to measure at least one further capacitance which is electrically coupled by a parasitic capacitance to the capacitance that is to be measured.

12. The endoscope as claimed in claim 1, wherein the evaluation device is configured to generate at least one of an acoustic or visual warning signal when the definable distance threshold value is undershot.

13. The endoscope as claimed in claim 12, wherein the at least one warning signal varies according to a distance such that a warning signal frequency is higher for a shorter distance between the endoscope and a ground adapted to be formed by a patient's body.

14. A method for preventing a collision between an endoscope and a patient's body, comprising:
- carrying out a measurement of a distance between the endoscope and at least one tissue of the patient's body outside a viewing region of the endoscope continuously using a proximity sensor provided at least at a distal end of a shaft of the endoscope;
- generating a warning signal when a threshold value defining a critical distance value from the tissue is attained or undershot; and
- in response to the warning signal, increasing the distance between the tissue and the endoscope.

15. The method as claimed in claim 14, further comprising using a capacitive sensor for the distance measurement, carrying out the measurement of the distance using the capacitive sensor by measuring a first capacitance between the proximity sensor and the tissue, and measuring at least one further capacitance which is electrically coupled by a parasitic capacitance to the first capacitance that is measured.

* * * * *